United States Patent
Maget

(10) Patent No.: US 6,413,238 B1
(45) Date of Patent: Jul. 2, 2002

(54) FLUID DISPENSER WITH STABILIZED FLUID FLOW

(75) Inventor: Henri J. R. Maget, La Jolla, CA (US)

(73) Assignee: Baxter International Inc, Deerfield, IL (US)

(*) Notice: Subject to any disclaimer, the term of this patent is extended or adjusted under 35 U.S.C. 154(b) by 0 days.

(21) Appl. No.: 09/397,944

(22) Filed: Sep. 17, 1999

(51) Int. Cl.$^7$ .......................... A61M 37/00; A61M 31/00
(52) U.S. Cl. .......................... 604/132; 604/505; 604/67
(58) Field of Search .......................... 604/131–133, 604/140, 141, 143–145, 151, 890.1, 891.1, 27, 28, 30, 31, 503–505, 65, 67, 93.01; 128/DIG. 12

(56) References Cited

U.S. PATENT DOCUMENTS

| | | | |
|---|---|---|---|
| 4,360,019 A | * 11/1982 | Portner et al. | 128/213 R |
| 4,781,688 A | * 11/1988 | Thoma et al. | 604/132 |
| 4,886,514 A | 12/1989 | Maget | |
| 4,902,278 A | 2/1990 | Maget et al. | |
| 5,707,361 A | * 1/1998 | Slettenmark | 604/131 |
| 5,848,991 A | * 12/1998 | Gross et al. | 604/140 |
| 5,928,194 A | 7/1999 | Maget | |
| 5,938,640 A | 8/1999 | Maget et al. | |

* cited by examiner

*Primary Examiner*—Sharon Kennedy
(74) *Attorney, Agent, or Firm*—James McClain

(57) ABSTRACT

A fluid dispensing device and its method of operation are disclosed. The device includes a feedback system which allows the device to respond in a timely and measured manner to changes in the dispensing flow rate of fluid from the device. The feedback system operates effectively even under conditions where the cause of increase or decrease in flow rate is not unequivocally known or reasonably capable of direct measurement. The device has a fluid reservoir which has an outlet which optionally may have a flow or pressure resistance unit incorporated, into the outlet, and an electric (preferably electrochemical) gas generation module or reversible pump which provides gas pressure to dispense the fluid from the reservoir. A sensor is provided for detection and measurement of an internal or external operating parameter which is indicative of flow rate of the fluid being dispensed. Feedback from the sensor (and associated signal processing unit) is used by a controller to control electric current to the gas generation module, with the current being adjusted by the controller to adjust the amount of gas produced in a manner which will prevent the flow rate of the dispensed fluid from exceeding desired maximum or minimum limits.

57 Claims, 2 Drawing Sheets

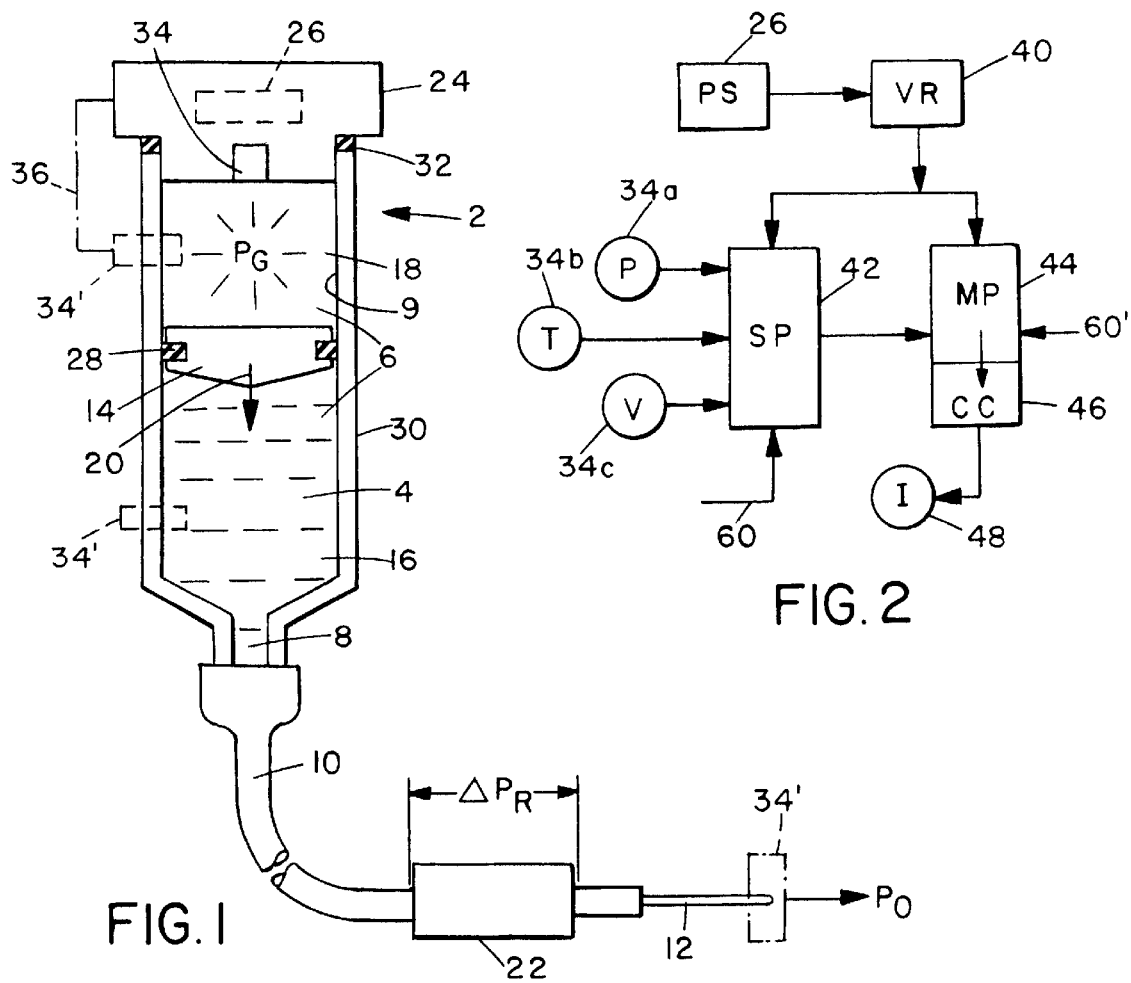
FIG. 1
FIG. 2
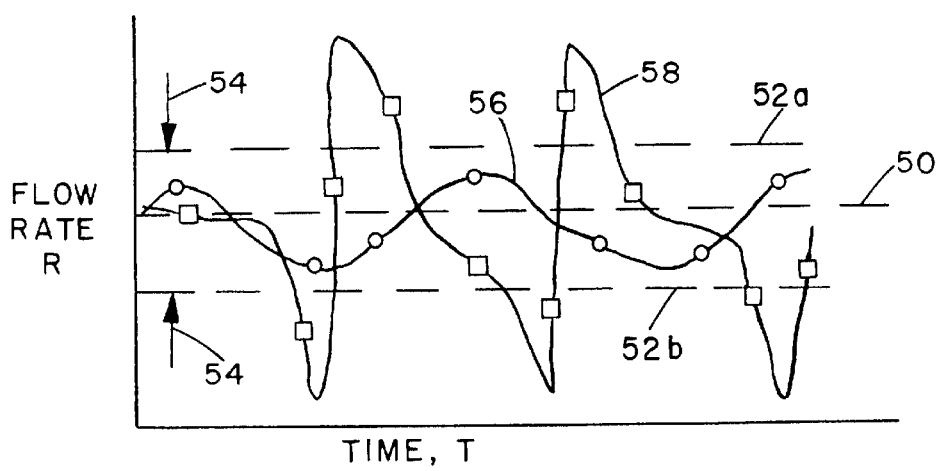
FIG. 3

FLUID DISPENSER WITH STABILIZED FLUID FLOW

BACKGROUND OF THE INVENTION

1. Field of the Invention

The invention herein relates to fluid dispensing devices in which a generated gas pressure causes discharge of fluid contained in the device over an extended period of time.

2. Description of the Prior art

Discharge of fluids from containers over extended periods of time is a necessity in many fields. For instance, many medications must be administered to patients in small, incremental doses over time, either continually or intermittently. Similarly, many chemical and biological processes and tests conducted in laboratories require prolonged infusion of reactants in small amounts over the course of the process or test. To meet this need, many devices have been introduced to the market which provide for intermittent or continual dispensing of liquid medications, reactants, and so forth. To dispense the liquids, some devices have included miniature electric liquid pumps, others have included miniature gas pressure generators, and some have relied on initial high gas pressure within the device. Among the devices which have been described or used have been those described in my prior U.S. Pat. Nos. 4,402,817; 4,522,698; 4,687,423; 4,886,514; 4,902,278; 5,038,821; 5,149,413; 5,788,682; 5,928,194 and 5,938,640.

Such prior devices have operated essentially on an "steady state" mode, so that if they are operating they are normally dispensing the liquid at what is intended to be a constant rate. However, in many operational situations the flow from the device becomes blocked or restricted, at least for part of the time, or needs to be varied according to internal or external parameters of the device or its environment. For instance, variations in back pressure from the target environment (such as intravenous or intraarterial pressure in a patient) will affect the flow rate of the dispensing device. In the past such changes in flow rate could only be compensated for by adjustment of a device manually, normally based on observation of the device's operation by the user or operator. Requiring manual correction or compensation of a device's operation is of course undesirable, because it is time consuming and requires constant or frequent attendance by the user or operator, and because in many cases changes in flow rate, particularly small ones, may not be observable by a user or operator until the cumulative effect of such small changes has become significant and perhaps harmful.

SUMMARY OF THE INVENTION

The present invention is of a fluid dispensing device which includes both a gas pressure generating device and an internal feedback system which allows the device to make changes in its own operation to respond in a timely and measured manner to changes, even small ones, in the dispensing flow rate of the fluid contained in the device. The feedback system operates effectively even under conditions where the cause of restriction or expansion of flow rate is not unequivocally known or reasonably capable of direct measurement.

The device of this invention comprises a fluid reservoir which has a fluid outlet which optionally may have a pressure or flow resistance unit incorporated into the outlet. It also has an electric gas generation module which generates a driving gas, preferably by electrochemical means, to provide gas pressure to force the contained fluid out of the reservoir through the outlet (and resistance unit, if present) to the target environment. The reservoir is divided into separate but adjoining chambers for the generated driving gas and for the fluid (liquid, vapor or gas) to be dispensed. The chambers are separated by a moveable fluid-tight partition, against which the gas pressure on one chamber is exerted, and which in response to such gas pressure, moves to force the fluid in the other chamber from the reservoir and out through a outlet, commonly a fluid conduit such as rigid or flexible tubing or a gas vent such as a grille.

Also present is a sensor for detecting and measuring a variable parameter which may be internal or external to the device, but which is related directly or inversely to the operation of the device and the discharge or dispensing of the fluid. Such a parameter may be physical, chemical or biological, such as, for instance, fluid pressure or volume within either chamber of the reservoir, discharge fluid flow rate or discharge fluid exit pressure, or concentration of a component of the fluid. The sensor sends a signal defining the rate, direction and/or magnitude of any change in that parameter to a controller which controls the electric current which operates the gas generation module. The quantity and rate of gas generation are thereby regulated by the controller's variation of the current operating the gas generation module, which in turn varies the gas pressure within the reservoir and thus the flow rate and quantity of the fluid which is dispensed, such dispensing thus being responsive to changes in the measured parameter.

The controller operates in response to signals from the sensor of changes in the measured parameter to control the electric current flow in a manner which causes the gas generation module to increase or decrease the module's gas generation rate so as to maintain fluid dispensing flow rate within prescribed limits.

Because the device therefore maintains substantial constant flow rate based on response to a specific internal or external parameter which is in some manner indicative of the fluid dispensing rate of the device, its control and operation are not dependent on detection or measurement of highly variable or difficultly measured system or target properties which are or may be the source of the change in the measured parameter. For instance, flow of fluid from a hypodermic syringe into a patient's artery or vein will be impeded or speeded up by changes in the patient's intraarterial or intravenous blood pressure. These pressures are difficult or cumbersome to detect and measure, but their effect on the fluid dispensing flow results in an increase or decrease in the gas pressure in the reservoir required to move the fluid against the intraarterial or intravenous pressure. Such gas pressure within the reservoir, in contrast, can be easily detected and measured by a sensor, when then can initiate the operations described above to adjust the electric current and gas generation rate to compensate for the variations in the intraarterial or intravenous pressure, notwithstanding that the latter have not been directly measured.

The fluid to be dispensed may be a liquid, such as a liquid medication, a vapor such as a scented vapor for indoor air freshening or a medicinal vapor such as for use as an inhalant by patients with breathing difficulties, or a gas such as an inhalant or a chemically reactive gas which is being dispensed for use in a chemical or biological process.

Therefore, in one embodiment the invention involves a fluid dispensing device comprising a housing having an internal fluid reservoir divided by a movable fluid-tight partition into first and second chambers on opposite sides of the partition; electrically operated gas generation module for generating gas and moving the gas into the first chamber and exerting pressure on the partition; liquid outlet means from the second chamber for dispensing of fluid contained in the second chamber under pressure from contact with the partition; sensor means for detection and measurement of an operational parameter of the device over time and generation of a signal indicating quantity and direction of any change in the parameter, such change in the parameter resulting in change to flow rate of liquid from the second chamber; and controller means responsive to the signal for adjusting electrical current to the module in a manner which will change gas pressure within the reservoir, whereby change in gas pressure induced by the current change is in a direction and amount sufficient to keep the liquid flow rate at any time from exceeding predetermined minimum and maximum values for the parameter.

In another embodiment, the invention involves a fluid dispensing device comprising a housing having an internal fluid chamber comprising a gas compartment and a liquid compartment separated by a moveable pressure responsive member, the liquid compartment having a restricted liquid outlet conduit providing liquid communication between the liquid compartment and an outlet end of the conduit, the outlet end opening to an exterior of the housing; pumping means comprising an electrochemical cell in gas communication with the gas compartment, for pumping gas into the gas compartment , which gas exerts pressure against the pressure responsive member causing responsive movement thereof into the liquid compartment, thereby causing liquid within the liquid compartment to move toward and through the liquid outlet conduit to the exterior of the housing; a pressure sensor for measurement of gas pressure in the gas compartment; detection means for determining liquid flow rate at the outlet end of the liquid outlet conduit; and current control means responsive to gas pressure measurement of the pressure sensor and liquid flow rate determination for adjusting of electrical current in the cell; whereby upon change in gas pressure or environmental temperature which results in change of the liquid flow rate at the outlet end of the liquid outlet conduit causes the current control means for adjusting the electrical current in the cell to increase or decrease the current and increase or decease the pumping of gas into the gas compartment, to return the liquid flow rate to a value pertaining immediately prior to the change in gas pressure or environmental temperature, such that over an operating period of the device fluid flow rate of the liquid being discharged through the outlet end of the liquid outlet conduit remains substantially constant.

In yet another embodiment, the invention involves a method of controlling fluid discharge rate from a fluid dispensing device which comprises providing a fluid dispensing device comprising a housing having an internal fluid chamber comprising a gas compartment and a liquid compartment separated by a moveable pressure responsive member, the liquid compartment having a restricted liquid outlet conduit providing liquid communication between the liquid compartment and an outlet end of the conduit, the outlet end opening to an exterior of the housing, and pumping means comprising an electrochemical cell in gas communication with the gas compartment, for pumping gas into the gas compartment, which gas exerts pressure against the pressure responsive member causing responsive movement thereof into the liquid compartment, thereby causing liquid within the liquid compartment to move toward and through the liquid outlet conduit to the exterior of the housing; measuring gas pressure in the gas compartment; determining liquid flow rate at the outlet end of the liquid outlet conduit; and in response to measured value of the gas pressure measurement and liquid flow rate, determining whether change in gas pressure or environmental temperature has occurred resulting in change of the liquid flow rate at the outlet end of the liquid outlet conduit, and thereupon increasing or decreasing electrical current in the cell, thereby respectively increasing or deceasing the pumping of gas into the gas compartment, as required to return the liquid flow rate to a value pertaining immediately prior to the change in gas pressure or environmental temperature, such that over an operating period of the device fluid flow rate of the liquid being discharged through the outlet end of the liquid outlet conduit remains substantially constant.

Other embodiments and aspects of the invention will be evident from the description below.

BRIEF DESCRIPTION OF THE DRAWINGS

FIG. 1 is a side elevation view of a device of this invention, exemplified as a syringe and liquid flow tube and dispensing needle, with the syringe shown partially cut away, and illustrating the structure of such device and its method of operation.

FIG. 2 is a block flow diagram illustrating the feedback control and operation of the device of this invention.

FIG. 3 is a graph illustrating typical feedback controlled flow rates over time of devices of this invention as compared to typical non-feedback controlled flow rates over time of prior art devices.

DETAILED DESCRIPTION AND PREFERRED EMBODIMENTS

Figure 4:
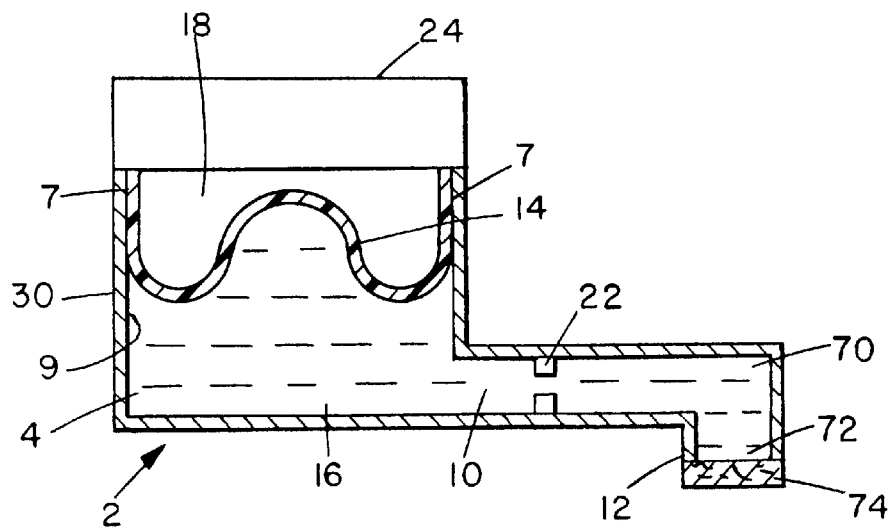
FIGS. 4 and 5 illustrate examples of alternative embodiments of the device of this invention and the methods of their operation.

The invention will be best understood by initial reference to the Figures. FIG. 1 illustrates a typical device 2 of this invention, exemplified as a syringe, for dispensing a fluid 4 from an internal reservoir 6 through outlet 8. Conveniently outlet 8 feeds into a conduit 10 which is terminated by a dispensing member 12 (illustrated as a hypodermic needle) for each in dispensing the fluid 4 to a target environment (not shown). Within the device 2 the reservoir 6 is divided by a moveable partition 14, in this case a plunger, into a fluid chamber 16 and a gas chamber 18. The target environment (typified by 3 in FIG. 6) may be a human being or animal, a body of chemical or biological material, a chemical or biological process, the ambient atmosphere or the like. The fluid 4 being dispensed may be a liquid, a gas or a vapor.

Plunger 14 is movable through the length of the reservoir 6, as indicated by arrow 20, under the influence of the gas pressure in chamber 18, to dispense the fluid 4 from the device 2. If desired, a restrictor 22 may be inserted into or attached at the end of the dispensing tubing 10 to provide a controlled and known resistance to flow of the fluid 4 or to back pressure changes from the target environment, such as changes in intravenous or intraarterial pressure in the patient.

A gas generation module 24 is mounted on the syringe 2 adjacent to and in fluid communication with the gas chamber 18 portion of the reservoir 6. The module is electrically operated, such as by a battery 26, to generate air, oxygen or other gas by electrochemical reactions to be described below, which gas is passed into chamber 18 and provides the gas pressure to motivate plunger 14 to move along the length of the reservoir 6 and force the liquid 4 to be dispensed from the device 2. Movement of plunger 14 results in continual change in the relative sizes of chambers 16 and 18 within the reservoir 6. Plunger 14 maintains its gas-tight property necessary to move under the influence of the gas in chamber 18 by means of a peripheral seal 28, such as an O-ring or X-ring. Similarly, gas generation module 24 is sealed in a gas-tight relationship with the barrel 30 of syringe 2 by a gasket 32.

Alternatively, gas generation module 24 can function as a reversible pump, acting to generate gas from an atmospheric source and pump it into the gas chamber 18 as described above, or to operate with reverse polarity of the current and move the gas in the opposite direction, i.e., to generate gas from the reservoir 6 as the source and discharge it on the opposite side of the module 24 to the atmosphere.

Details of the construction and operation of such modules/pumps (also referred to as electrochemical cells) will be found in one or more of my patents mentioned above. The same or similar devices are applicable in this case. All of the module/pump/cell devices mentioned in my prior patents can be used in this invention, since all can be controlled by the feedback-responsive control system of the present invention.

Sensor 34 measures an operationally-relevant physical, chemical or biological parameter. Those skilled in the art will readily be able to determine the optimum or most convenient operationally-related parameter to use as the control parameter in any system using a device 2 of this invention. For example, in the device and system illustrated in FIG. 1, one can detect and measure one or more of fluid pressure within the gas chamber 18 or the fluid chamber 16, fluid pressure $P_O$ at the exit of the fluid outlet 12, concentration of a component of the fluid, pressure drop $\Delta P_P$ across the plunger 14, temperature within the reservoir 6, volume of the fluid 4 within the fluid chamber 16, volume rate of discharge of the fluid 4 from the fluid chamber 16 or the fluid outlet 12 or strain in a wall of the housing or barrel 30 defining the reservoir 6. Various alternative locations may be used, as indicated by 34', depending on the specific parameter or parameters selected for control. (If there are multiple control parameters, one of the functions of the sensor 34 and/or controller 44 will be conflict resolution to determine which parameter will control if conflicting signals from multiple sensors are received.

In the embodiment shown in FIG. 1, it is generally preferred that sensor 34 be a pressure sensor, either measuring the gas pressure $P_G$ of the gas in chamber 18 or the fluid pressure $P_F$ within the fluid chamber 16 of the reservoir 6. Conveniently sensor 34 is directly integrated into module 24 as shown, but alternatively it may be mounted separate from module 24 but still with fluid communication with the interior of gas chamber 18, as shown at the upper 34', and connected to module 24 by wires 36, or in fluid communication with the interior of fluid chamber 16, as shown at the middle 34', and connected to module 24 by wires (not shown) in the manner just mentioned.

For description herein of the operation of the device, the following nomenclature will be used:

$P_G$ or P=the gas pressure within the gas chamber 18 of the reservoir 6; this is the pressure of the gas generated by module 24;

$\Delta P_P$=the pressure drop across the plunger 14; $P_F$=the fluid pressure within the fluid chamber 16 of the reservoir 6; this is the pressure $P_G$ or P of the gas generated by module 24 less $\Delta P_P$;

$P_O$=the outlet pressure of the fluid 4 at its contact with the target environment, such as at the outlet end of hypodermic needle 12;

$\Delta P_R$=the pressure drop in the liquid across the restrictor 22, if one is present;

R=the flow rate of the liquid 4;

T=ambient temperature of the gas and liquid;

I=the current operating the gas generation module 24;

V=volume of the liquid 4 in the chamber 16 of the reservoir 6;

All parameters are defined in conventional and consistent units.

The device's operation is based on the underlying relationship $$P_G = P_O + P_R + \Delta P_P = P_F + \Delta P_P$$

because the pressure drop within the tubing 10 can be considered to the negligible as compared to these pressure and pressure drop values.

Further, for the purposes of feedback operation, two derived coefficients, α and β, must be defined. α is a coefficient derived from Faraday's Law, affecting the fluid flow rate in the following manner:

$$R = (\alpha I)/P$$

describing the correlation between the rate of gas generation and the electrochemical current. Since a gas is generated, α is temperature-dependent.

Under steady state conditions a is defined as $$\alpha = (R/I)(P_G + (R/\beta))$$

β, in turn, is a correlation between the restrictor pressure drop and the fluid flow rate, and is defined as:

$$\beta = R/(P_F - P_O), \text{ or}$$

$$\beta = (k/\mu)(R/(P_F - P_O)),$$

where k is a constant dependent on the restrictor dimensions (i.e., diameter and length) and μ is the fluid viscosity at the ambient temperature. It will be seen that both α and β are temperature dependent. It will also be seen that if no restrictor is present, $P_F - P_O$ approaches 0 (the negligible tubing pressure drop being the difference) and β approaches ∞ or is undefined.

The overall operation of the system is illustrated FIG. 2. A power source (battery 26) operates a voltage regulator 40 incorporated into the electronics of the gas generation module 24. The signal processor 42 also in the module 24 receives input from one or more parameter sensors 34 which may sense gas pressure P (at 34a), reservoir temperature T (at 34b), or electrochemical cell voltage V (at 34c). Other input variables such as gas or liquid volume may also be used as the sensed parameter, such as by determining the position of plunger 14 with respect to either end of the reservoir 6. Signal processor 42 if necessary may also serve as an analog to digital converter. Information from signal processor 42 based on the signals received from the parameter sensors 34 is transmitted to microprocessor 44 which in turn determines the new appropriate current I for the electrochemical module 24 and operates current controller 46 to adjust the current I at 48 so that the module 24 thereafter operates at the new current and the flow rate R is maintained within the desired range.

A typical motive operation is illustrated in FIG. 3. Because $P_O$ is rarely constant for prolonged periods of time, it is not practical to try to maintain the flow rate R at a constant value such as indicated at 50. Rather an acceptable maximum flow rate 52a and minimum of flow rate 52b are determined, which define a range indicated by the arrows 54. The optimum flow rate 50 may or may not be at the center of the defined range, depending on the relative significance of higher and lower flow rates to the desired operation of the device. Thereafter the system normally operates as indicated by the generalized curve 56 which fluctuates within the defined range. Also shown for comparison is a generalized curve 58 which represents schematically prior art devices in which changes in $P_O$ which cannot be compensated for by those devices cause the plunger 14 to stop and then subsequently be forced into motion abruptly by a substantial increase in pressure P, which leads to extreme fluctuations in flow rate as indicated by the curve 58.

The restrictor 22 is normally a fixed value restrictor such as of a piece of tubing of smaller diameter than tubing 10, which is cut to the appropriate length so that the overall desired pressure drop $\Delta P_R$ is obtained. The restrictor is selected so as to minimize the effect of change in the several variables on the overall flow rate.

Figure 5:
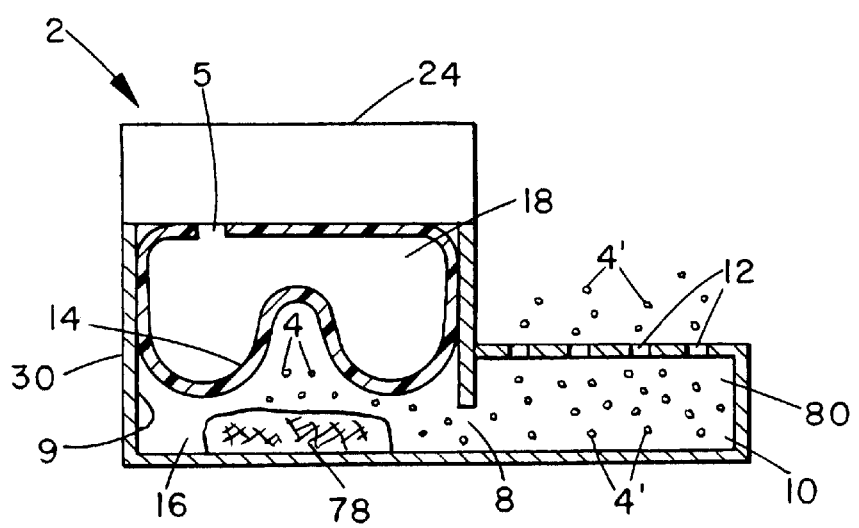

The pressure drop across the plunger 14 ($\Delta P_P$) is usually a significant variable, since the frictional forces of a plunger vary with lubricity, barrel diameter, temperature, pressure, age, and material properties of the material from which the plunger is made. The control system of the present invention to a significant extent is intended to provide automatic compensation for variation in the plunger's operation. FIGS. 4 and 5 illustrate exemplary alternative embodiments of the present invention. (In these Figures the actual device is illustrated in simplified form.) In FIG. 4 the partition 14 is shown as a flexible gas-tight sheet, preferably of a rubber or elastomeric material, attached to the interior wall 9 of the barrel or housing 30 at 7, to form gas chamber 18 and fluid chamber 16. Addition of gas into chamber 18 causes the sheet 14 to move toward the outlet 8 and force the fluid 4 from the chamber 16 through conduit 10 to dispensing member 12. A restrictor 22 may be present as indicated above. In this embodiment the dispensing member 12 is illustrated as a fibrous or porous dispensing pad 74 attached below outlet 72. Fluid 4 (such as a liquid medication for topical administration to a patient) flows in a controlled manner into chamber 70 from which it flows through outlet 72 onto pad 74. The device 2 may be placed on the surface of a patient's skin with the pad 74 in contact with the skin. The medicinal fluid 4 then flows or diffuses through the pad 74 onto the patient's skin, and passes transdermally into the patient, or spreads topically across the surface of the patient's skin.

In the embodiment shown in FIG. 5, the gas chamber 18 is illustrated as an inflatable bag or balloon which is disposed within reservoir 6 but normally is not attached to the interior walls of the barrel or housing 6. There is a fluid connection between the gas generation module 24 and the interior of the bag or balloon 18 through gas valve 5. As the bag or balloon 18 inflates, it expands within the reservoir 6, pressure seals against the interior wall 9 of the housing or barrel 30 to define fluid chamber 16, and forces the fluid 4 out of chamber 16 through outlet 8 into conduit 10. In FIG. 5 the dispensing fluid 4 is illustrated as a vapor 4' which is emitted from a material or container 78. Emission may be caused in a number of ways. For instance, the container 78 may be a thin-walled glass vial with the vapor inside, with the vapor 4' released when the vial is broken, as by shaking the device 2 or by the increasing pressure in chamber 16 from inflation of bag or balloon 18; the material 78 may by susceptible to heating to give off the vapor 4' (heat may be applied exteriorly to the device, or internally in chamber 16 by a heating element, not shown); a liquid such as water may be injected into chamber 16 (by means not shown) to cause the material 78 to react and evolve the vapor 4'; and so forth.

In the FIG. 5 embodiment the dispensing member 12 is a vent or grille through which the vapor 4' exhausts. The vapor 4' may exhaust into the ambient atmosphere, as where the vapor is intended to provide scent, moisture, static electricity control, or other property to the atmosphere. Alternatively the exhaustion may be into a chemical or biological reaction chamber, vessel or the like, where the vapor provides, for example, an inert atmosphere, a reactant or a coating material.

The evolved fluid 4' in the FIG. 5 embodiment may alternatively be a gas, such as oxygen, nitrogen, argon, carbon dioxide, etc. Evolution may be from a vial 78, as discussed above, or from physical or chemical reaction of the material 78. Of course whether the fluid 4 is a gas or vapor, it usually will be inert to the materials of the device 2 itself, such as the partition 14, so that operation of the device 2 will not be adversely affected. Where the device 2 is be considered dispensable, the fluid 4 need not be inert to the materials of the device, as long as the attack by the fluid 4 is sufficiently slow that the desired quantity of the fluid 4 is dispensed before the device 2 fails.

An important element of the present invention is that it can be independent of the necessity of external measurement of the parameters of the target environment. This means that is not necessary to independently determine the value of $P_O$ in order to manually adjust the operation of the device 2, because $P_O$ is part of the difference equation above. Since element $\Delta P_R$ in the equation is known and element $P_G$ is measured by the sensor 34, and with the acceptable flow rate range illustrated in FIG. 3 being predetermined, the change in $P_O$ is automatically compensated for by the overall feedback system of the present invention, without any needed to independently measure $P_O$. This feature is valuable when the environment where $P_O$ exists makes it difficult or inadvisable to position a sensor 34 at that location.

Figure 6:
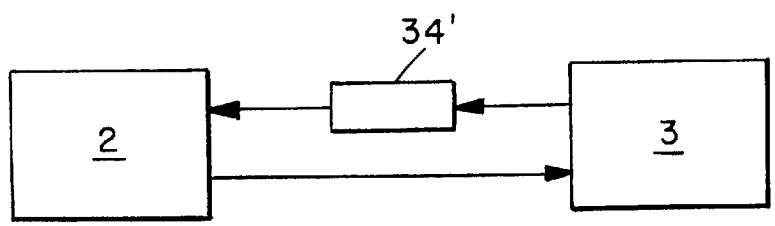
FIG. 6 illustrates schematically the use of a controlling parameter external to a device of this invention.

Notwithstanding the above, the invention is sufficiently versatile that if desired it need not be directly controlled by one of the internal system variables itself, but can be controlled by an external parameter, as indicated in FIG. 6. For instance, if the device 2 is being used to deliver medication to a patient (indicated at 3), it may be desirable to operate the system based on the delivered dosage or the effect on one or more of the patient's bodily systems. Similarly, if the device 2 is being used for delivery of chemicals or biological agents to a chemical or biological process (alternatively indicated at 3), the system may be run on the basis of measured changes in the process parameters. This type of operation can be accomplished by use of one or more separate features. For instance, in some cases it may be possible to program the microprocessor 44 to contain a correlation between the patient's response, the chemical process' parameter change, or some other external variable and the measured internal parameter (e.g., gas pressure), such that when the signal processor 42 receives the reading 34a of the pressure sensor 34 (34' in FIG. 6), the microprocessor 44 interprets that reading in response to the preprogrammed correlation and operates current controller 46 to change the current 48 based on the correlation rather than on the direct reading of the internal gas pressure. In another embodiment, it may be necessary to have an external sensor implanted in or attached to a patient or incorporated into a chemical or biological process, which external sensor sends an external signal 60 to the signal processor 42 or an external signal 60' to the microprocessor 44, and that signal is processed along with the sensed parameter signal from sensor 34 through a correlation incorporated into microprocessor 44 between the internal signal from sensor 34 and external signal 60 or 60', to generate the appropriate signal from microprocessor 44 to control current controller 46.

The versatility of the present invention is illustrated in tabular form in the Table below. This Table illustrates the three principal variables that are most commonly used for the present invention, i.e., pressure P, system temperature as affecting the coefficient $\alpha$, or system temperature as affecting the coefficient $\beta$. The arrows in the Table graphically illustrate whether a variable, effect or correction involves an increase (), a decrease () or no change (→). The six conditions listed illustrate respectively an increase or decrease in pressure, an increase or decrease in temperature or $\alpha$, and an increase or decrease in temperature or $\beta$, with the resulting effects, if any, on gas pressure P, liquid pressure, restrictor pressure or flow rate such changes, and the automatic feedback correction of the present system of resulting in the change in current to the module 24 to move the system back toward the optimum flow rate. It will be evident that this Table is exemplary only and that an equivalent table can readily be determined by those skilled in the art for other variables such as liquid volume. In each of the six cases illustrated only one variable at a time has been changed. It will also be evident that a similar table can readily be drawn for changes in two or more variables simultaneously, whether changes are in the same direction (i.e., both increasing or decreasing) or in opposite directions.

allowable width of the acceptable operating range (FIG. 3). A narrow acceptable range will require a sensor 34 of high sensitivity to changes in the measured variable while a wide operating range will allow for use of a less sensitive sensor. Similar degrees of sensitivity can be built or programmed into the signal processor 42 or the microprocessor 44.

It will be evident that there are numerous embodiments of this invention which include variations from the example described above and shown in the Figures. For instance, in the embodiment exemplified, the pressure-driven member which contacts the liquid 4 and forces it out of the reservoir is plunger 14. However, it is entirely suitable to substitute a flexible diaphragm or a gas driven piston for plunger 14. Similarly, sensor 34 is shown (either at 34 or 34') positioned to measure gas pressure $P_G$ in the chamber 18. Alternatively, however, one can position sensor 34 within liquid 4 in chamber 16 and measure the water pressure. Positioning of sensors to measure other operating parameters will also be readily understood by those skilled in the art. One may also have a separate sensor to measure $\Delta P_R$ across the restrictor 22. Also, although one of the features of this invention is that it operates without measurement of $P_O$ directly, but if the target environment permits, it may be found convenient to have a sensor to measure $P_O$ directly, especially if the user or operator of the device wishes to create a record of $P_O$ over time.

There may be a number of other devices, accessories and the like incorporated into the system, such as signals or alarms for low battery voltage, electrochemical cell overvoltage, overpressure within the reservoir, cumulative amount of fluid delivered at any time, and so forth.

The invention herein uniquely provides for controlled and controllable generation of a gas to produce movement of the liquid, gas or vapor instantaneously and on demand. In effect the electrochemical module 24 serves as a controllable

TABLE

RESPONSES TO CHANGES IN VARIABLES

| | VARIABLES | | | EFFECTS | | | |
|---|---|---|---|---|---|---|---|
| | | | | GAS | LIQUID | RESTRICTOR | CORRECTION |
| CONDITION | PRESSURE $P_O + \Delta P_P$ | TEMPERATURE AS AFFECTING $\alpha$ | TEMPERATURE AS AFFECTING $\beta$ | PRESSURE, $P_G$ | PRESSURE, $P_L$ | PRESSURE OR FLOWRATE | CHANGE IN CURRENT, I |
| 1 | ↗ | → | → | ↗ | ↗ | ↘ | ↗ |
| 2 | ↘ | → | → | ↘ | ↘ | ↗ | ↘ |
| 3 | → | ↗ | → | ↗ | ↗ | ↗ | ↘ |
| 4 | → | ↘ | → | ↘ | ↘ | ↘ | ↗ |
| 5 | → | → | ↗ | ↘ | ↘ | ↗ | ↘ |
| 6 | → | → | ↘ | ↗ | ↗ | ↘ | ↗ |

It will be evident from the Table that the feedback mechanism of the present invention operates continually and in a timely manner to deal with any fluctuations in the sensed parameter, e.g., gas pressure, which is being used as the control parameter. Undesirable wide control fluctuations are avoided, since the sensor 34 promptly reacts to each change in the sensed parameter, sends the appropriate signal to be signal processor 42, which in turn sends interpreted information to the microprocessor 44, which adjusts the current controller 46 to keep the module 24 operating at essentially the optimum control point. Sensitivity of the system to changes can be predetermined by whether or not a restrictor 22 is in the system, what the degree of pressure drop of that restrictor is, or what the preset degree of sensitivity is of sensor 34. These selections are effectively determined by the microprocessor in which the variable gas output is dependent upon the current input, and current input in turn is determined by feedback from the system itself through sensing of pressure or another operating parameter.

Devices of this invention will find use in many fields and applications. They can be used as fluid administration devices for placement on, adjacent to or within a human or animal body, tissue, bone or organ, to deliver pharmaceutical, physiological, curative, medicinal, homeopathic, nutritive or anesthetic fluids to a human being or animal; dispense chemicals or biological materials; emit gases and vapors to increase, enhance or control properties of the ambient atmosphere; or the like. Those skilled in the art will recognize numerous other applications and fields of use.

It will be evident to those skilled in the art that there are numerous embodiments of the present invention which, while not specifically described above, are clearly within the scope and spirit of the invention. The above description is therefore intended to be exemplary only, and the scope of the invention is to be determined solely from the appended claims.

I claim:

1. A fluid dispensing device comprising:
   a housing having an internal fluid reservoir divided by a movable fluid-tight partition into first and second chambers on opposite sides of said partition;
   electrically operated gas generation/extraction module for moving a gas into or out of said first chamber, said gas therein exerting or reducing pressure on said partition;
   controllable source of electric current for operation of said module, said source connected to a controller for controlling said source to vary the amount or polarity or both of said electrical current to said module and thereby operate said module to change its rate of gas generation or extraction, said controller being responsive to a measurable parameter associated with said device;
   fluid outlet from said second chamber for dispensing of fluid contained in said second chamber exteriorly of said device in response to said pressure on said partition; and
   sensor means for detection and measurement of said parameter over time and generation of a signal to said controller indicating quantity and direction of any change in said parameter, said controller in response to said signal indicating said change in said parameter varying said electric current to said module to effect said change in rate of gas generation or extraction;
   whereby said change in said rate of gas generation or extraction effects a change in gas pressure in said first chamber and resultant change in said pressure on said partition, said pressure change being in a direction and amount sufficient to keep said fluid flow from said second chamber at any time from exceeding predetermined minimum and maximum values of said parameter.

2. A device as in claim 1 wherein said sensor detects and measures a physical, chemical or biological parameter.

3. A device as in claim 2 wherein said sensor detects and measures a parameter comprising at least one of fluid pressure within said first chamber or said second chamber, fluid pressure at an exit of said fluid outlet, concentration of a component of said fluid, pressure drop across said partition, temperature within said reservoir, volume of said fluid within said second chamber, volume rate of discharge of said fluid from said second chamber or said fluid outlet or strain in a wall of said reservoir.

4. A device as in claim 2 wherein said parameter exists at a location exteriorly of said device and said sensor is disposed exteriorly of said device to detect and measure said parameter.

5. A device as in claim 4 wherein said sensor detects and measures a parameter comprising a reaction condition of a chemical or biological reaction to which said fluid is dispensed, a bodily condition of a human being or animal to whom said fluid is being administered, an ambient environmental condition adjacent to said device, or a property of dispensed fluid at a location exteriorly of said device.

6. A device as in claim 1 wherein said sensor is disposed between said gas generation module and said first chamber or fully or partially in said first chamber or said second chamber or at an exit of said fluid outlet.

7. A device as in claim 1 wherein said second chamber contains a gas, a vapor or a vapor- or gas-emitting substance and said fluid dispensed from said second chamber comprises gas or vapor.

8. A device as in claim 1 wherein said second chamber contains a liquid or a liquid-emitting substance and said fluid dispensed from said second chamber comprises liquid.

9. A device as in claim 1 wherein said controller comprises a microprocessor.

10. A device as in claim 1 wherein said moveable partition comprises plunger, a piston head or a flexible sheet.

11. A fluid dispensing device comprising:
    a housing having an internal fluid chamber comprising a gas chamber and a fluid chamber separated by a moveable pressure responsive partition, said fluid chamber having a fluid conduit providing fluid communication between said fluid liquid chamber and an outlet end of said conduit, said outlet end opening to an exterior of said housing;
    pumping means comprising an electrochemical cell in gas communication with said gas chamber, for pumping gas into or out of said gas chamber, said gas when in said chamber exerting pressure against said pressure responsive partition causing responsive movement thereof of fluid in said liquid chamber, said responsive movement comprising said fluid moving toward and through said fluid conduit to said exterior of said housing or being withdrawn from said conduit into said liquid chamber;
    controllable source of electric current for operation of said pumping means, said source connected to a controller for controlling said source to vary the amount and polarity of said electrical current to said pumping means and thereby operate said pumping means to change its rate or direction of pumping of said gas, said controller being responsive to a measurable parameter associated with said device; and
    sensor means for detection and measurement of said parameter overtime and generation of a signal to said controller indicating quantity and direction of any change in said parameter, said controller in response to said signal indicating said change in said parameter varying said electric current to said module to effect said change in rate of gas generation;
    whereby upon said change in said measured parameter, said controller regulates said amount and polarity of said electrical current to said pumping means to increase or decease rate of pumping of said gas or change direction of pumping of said gas, such that fluid flow to or from said fluid chamber rate maintains a cumulative total of said fluid discharged from said fluid chamber to a target environment over a selected period of time to be within a predetermined range.

12. A device as in claim 11 wherein said sensor detects and measures a physical, chemical or biological parameter.

13. A device as in claim 12 wherein said sensor detects and measures a parameter comprising at least one of fluid pressure within said gas chamber or said fluid chamber, fluid pressure at an exit of said fluid chamber, concentration of a component of said fluid, pressure drop across said partition, temperature within said reservoir, volume of said fluid within said fluid chamber, volume rate of discharge of said fluid from said fluid chamber or said fluid outlet or strain in a wall of said reservoir.

14. A device as in claim 11 wherein said sensor is disposed between said pumping means and said gas chamber or fully or partially in said gas chamber or said fluid chamber or at an exit of said fluid chamber.

15. A device as in claim 11 wherein said parameter exists at a location exteriorly of said device and said sensor is disposed exteriorly of said device to detect and measure said parameter.

16. A device as in claim 15 wherein said sensor detects and measures a parameter comprising a reaction condition of a chemical or biological reaction to which said fluid is dispensed, a bodily condition of a human being or animal to whom said fluid is being administered, an ambient environmental condition adjacent to said device, or a property of dispensed fluid at a location exteriorly of said device.

17. A device as in claim 11 wherein said fluid chamber contains a gas, a vapor or a vapor- or gas-emitting substance and fluid dispensed from said fluid chamber comprises gas or vapor.

18. A device as in claim 11 wherein said fluid chamber contains a liquid or a liquid-emitting substance and said fluid dispensed from said fluid chamber comprises liquid.

19. A device as in claim 11 wherein said controller comprises a microprocessor.

20. A device as in claim 11 wherein said moveable partition comprises plunger, a piston head or a flexible sheet.

21. A device as in claim 11 comprising a syringe.

22. A device as in claim 21 wherein said syringe comprises a elongated hollow cylindrical body having a first end and an opposite second end, and said moveable pressure responsive partition comprises a moveable plunger within said hollow cylindrical body and disposed intermediate said first and second ends, that portion of said body adjacent said first end comprising said gas compartment and that portion of said body adjacent said second end comprising said fluid compartment, with said plunger separating said compartments.

23. A device as in claim 22 further comprising said pumping module comprising said electrochemical cell being disposed in said first end such that gas generated by said electrochemical cell is pumped directly into said gas compartment.

24. A device as in claim 23 further comprising said pressure sensor being disposed at an interface between said pumping module and said gas chamber.

25. A device as in claim 22 further comprising said plunger being moveable longitudinally of said hollow cylindrical body, such that longitudinal movement of said plunger toward said second end of said body acts to expel fluid contained within said fluid compartment from said compartment through a fluid outlet conduit, flow rate of expelled fluid through said outlet end being determined by the pressure of said gas in said gas chamber exerting motivating force against said plunger to effect said longitudinal movement.

26. A device as in claim 25 wherein said fluid outlet conduit comprises an hollow elongates flexible tube.

27. A device as in claim 26 wherein at said outlet end of said conduit is disposed a hollow needle or cannula through which fluid expelled from said device can be injected into a human or animal.

28. A method for dispensing fluid from a fluid-containing device comprising:
providing a fluid dispensing device comprising:
a housing having an internal fluid reservoir divided by a movable fluid-tight partition into first and second chambers on opposite sides of said partition;
electrically operated gas generation module for generating gas and moving said gas into said first chamber, said gas therein exerting pressure on said partition;
controllable source of electric current for operation of said module, said source connected to a controller for controlling said source to vary the amount of said electrical current to said module and thereby operate said module to change its rate of gas generation, said controller being responsive to a measurable parameter associated with said device;
fluid outlet from said second chamber for dispensing of fluid contained in said second chamber exteriorly of said device in response to said pressure on said partition; and
sensor means for detection and measurement of said parameter over time and generation of a signal to said controller indicating quantity and direction of any change in said parameter, said controller in response to said signal indicating said change in said parameter varying said electric current to said module to effect said change in rate of gas generation;
operating said sensor such that said sensor detects a change in said parameter over a period of time and generates said signal to said controller;
operating said controller such that said controller decreases or increases said amount of current or changes polarity of said current, said decrease, increase or change in polarity effecting a change in gas pressure in said first chamber and resultant change in said pressure on said partition, such that fluid flow rate from said second chamber at any time is maintained within predetermined minimum and maximum values.

29. A method as in claim 28 wherein said parameter detected and measured by said sensor comprises a physical, chemical or biological parameter.

30. A method as in claim 29 wherein said parameter comprises at least one of fluid pressure within said first chamber or said second chamber, fluid pressure at an exit of said fluid outlet, concentration of a component of said fluid, pressure drop across said partition, temperature within said reservoir, volume of said fluid within said second chamber, volume rate of discharge of said fluid from said second chamber or said fluid outlet or strain in a wall of said reservoir.

31. A method as in claim 28 wherein said parameter exists at a location exteriorly of said device, said method further comprising disposing said sensor exteriorly of said device to detect and measure said parameter.

32. A method as in claim 31 wherein said parameter comprises a reaction condition of a chemical or biological reaction to which said fluid is dispensed, a bodily condition of a human being or animal to whom said fluid is being administered, an ambient environmental condition adjacent to said device, or a property of dispensed fluid at a location exteriorly of said device.

33. A method as in claim 28 wherein said second chamber contains a gas, a vapor or a vapor- or gas-emitting substance and said fluid dispensed from said second chamber comprises gas or vapor.

34. A method as in claim 28 wherein said second chamber contains a liquid or a liquid-emitting substance and said fluid dispensed from said second chamber comprises liquid.

35. A method as in claim 28 wherein said controller comprises a microprocessor.

36. A method as in claim 28 wherein said device comprises a syringe.

37. A method as in claim 28 wherein said device comprises a transdermal administration device.

38. A method as in claim 28 wherein said device comprises a fluid administration device for placement on, adjacent to or within a human or animal body, tissue, bone or organ.

39. A method as in claim 28 further comprising said fluid being dispensed comprising a fluid having pharmaceutical, physiological, curative, medicinal, homeopathic, nutritive or anesthetic properties when administered to a human being or animal.

40. A method as in claim 28 wherein said fluid is dispensed through an outlet conduit comprising an hollow tube or a vent.

41. A method as in claim 28 wherein at said outlet end of said hollow tube is disposed a hollow needle or cannula through which fluid dispensed from said device can be injected into a human or animal.

42. A method as in claim 28 wherein at said outlet end of said hollow tube is disposed an administration pad through which fluid dispensed from said device can be administered to a human or animal transdermally or by direct application to an organ, tissue or bone.

43. A method for dispensing fluid from a fluid-containing device comprising:

providing a fluid dispensing device comprising:
a housing having an internal fluid chamber comprising a gas chamber and a fluid chamber separated by a moveable pressure responsive partition, said fluid chamber having a fluid conduit providing fluid communication between said fluid liquid chamber and an outlet end of said conduit, said outlet end opening to an exterior of said housing;
pumping means comprising an electrochemical cell in gas communication with said gas chamber, for pumping gas into or out of said gas chamber, said gas when in said chamber exerting pressure against said pressure responsive partition causing responsive movement thereof of fluid in said liquid chamber, said responsive movement comprising said fluid moving toward and through said fluid conduit to said exterior of said housing or being withdrawn from said conduit into said liquid chamber;
controllable source of electric current for operation of said pumping means, said source connected to a controller for controlling said source to vary the amount and polarity of said electrical current to said pumping means and thereby operate said pumping means to change its rate or direction of pumping of said gas, said controller being responsive to a measurable parameter associated with said device; and
sensor means for detection and measurement of said parameter over time and generation of a signal to said controller indicating quantity and direction of any change in said parameter, said controller in response to said signal indicating said change in said parameter varying said electric current to said module to effect said change in rate of gas generation;

operating said sensor to detect and measure said change in said parameter and send a signal thereof to said controller;
operating said controller upon receipt of said signal to regulate said amount and polarity of said electrical current to said pumping means to increase or decease rate of pumping of said gas or change direction of pumping of said gas, such that fluid flow to or from said fluid chamber rate maintains a cumulative total of said fluid discharged from said fluid chamber to a target environment over a selected period of time to be within a predetermined range.

44. A method as in claim 43 wherein said parameter detected and measured by said sensor comprises a physical, chemical or biological parameter.

45. A method as in claim 44 wherein said parameter comprises at least one of fluid pressure within said gas chamber or said fluid chamber, fluid pressure at an exit of said fluid chamber, concentration of a component of said fluid, pressure drop across said partition, temperature within said reservoir, volume of said fluid within said fluid chamber, volume rate of discharge of said fluid from said fluid chamber or said fluid outlet or strain in a wall of said reservoir.

46. A method as in claim 44 wherein said parameter exists at a location exteriorly of said device, said method further comprising disposing said sensor exteriorly of said device to detect and measure said parameter.

47. A method as in claim 46 wherein said parameter comprises a reaction condition of a chemical or biological reaction to which said fluid is dispensed, a bodily condition of a human being or animal to whom said fluid is being administered, an ambient environmental condition adjacent to said device, or a property of dispensed fluid at a location exteriorly of said device.

48. A method as in claim 43 wherein said fluid chamber contains a gas, a vapor or a vapor- or gas-emitting substance and fluid dispensed from said fluid chamber comprises gas or vapor.

49. A method as in claim 43 wherein said fluid chamber contains a liquid or a liquid-emitting substance and said fluid dispensed from said fluid chamber comprises liquid.

50. A method as in claim 43 wherein said controller comprises a microprocessor.

51. A method as in claim 43 wherein said device comprises a syringe.

52. A method as in claim 43 wherein said device comprises a transdermal administration device.

53. A method as in claim 43 wherein said device comprises a fluid administration device for placement on, adjacent to or within a human or animal body, tissue, bone or organ.

54. A method as in claim 43 further comprising said fluid being dispensed comprising a fluid having pharmaceutical, physiological, curative, medicinal, homeopathic, nutritive or anesthetic properties when administered to a human being or animal.

55. A method as in claim 43 wherein said fluid is dispensed through an outlet conduit comprising an hollow tube or a vent.

56. A method as in claim 43 wherein at said outlet end of said hollow tube is disposed a hollow needle or cannula through which fluid dispensed from said device can be injected into a human or animal.

57. A method as in claim 43 wherein at said outlet end of said hollow tube is disposed an administration pad through which fluid dispensed from said device can be administered to a human or animal transdermally or by direct application to an organ, tissue or bone.

* * * * *